United States Patent [19]
Koller et al.

[11] Patent Number: 5,416,260
[45] Date of Patent: May 16, 1995

[54] HOMOLOGOUS RECOMBINATION FOR UNIVERSAL DONOR CELLS AND CHIMERIC MAMMALIAN HOSTS

[75] Inventors: Beverly H. Koller, Carrboro; Oliver Smithies, Chapel Hill, both of N.C.

[73] Assignee: University of North Carolina at Chapel Hill, Chapel Hill, N.C.

[21] Appl. No.: 611,020

[22] Filed: Nov. 9, 1990

Related U.S. Application Data

[63] Continuation-in-part of Ser. No. 431,872, Nov. 6, 1989, abandoned, and a continuation-in-part of Ser. No. 385,651, Jul. 25, 1989, abandoned.

[51] Int. Cl.⁶ .................. C12N 15/00; C12N 5/00
[52] U.S. Cl. ..................... 800/2; 435/172.3; 435/240.2; 435/320.1; 435/317.1; 800/DIG. 1; 800/DIG. 2; 800/DIG. 3; 935/70; 935/111
[58] Field of Search ............ 435/172.3, 2, 317.1, 435/240.2, 320.1; 800/2, DIG. 1, DIG. 2, DIG. 3; 935/53, 70, 111

[56] References Cited

PUBLICATIONS

Thomas and Capecchi (1987), Cell, 51:503–512.
Mansour, et al. (1988) Nature 336:348–352.
Nandi, et al. (1988) P.N.A.S. 85:3845–3849.
Thomas, et al. (1986) Cell 44:419–428.
Song, et al. (1987) P.N.A.S. 84:6820–6824.
Ayares, et al. (1987) M.C.B. 7:1656–1662.
Ayares, et al. (1985) Genetics 111:375–388.
Wake, et al. (1985) M.C.B. 8:2080–2089.
Smithies, et al. (1985) Nature 317:230–234.
Kucherlapati, et al. (1985) M.C.B. 5:714–720.
Kucherlapati, et al. (1984) P.N.A.S. 81:3153–3157.
Gossler et al., Proc. Natl. Acad. Sci. 83: 9065–9069 (1986).
Joyner et al., Nature 338: 153–156 (1989).
Doetschman et al., Proc. Natl. Acad. Sci. 85: 8583–8587 (1988).
Doetschman et al., Nature 330: 576–578 (1987).
Parnes et al., Cell 29: 661–669 (1982).
Zimmer et al., Nature 338: 150–153 (1989).
Thomas et al., Cell 51: 503–512 (1987).
Saiki et al., Nature 324: 163–166 (1986).
Sullivan, et al. (1985) J. Clin. Invest. 76:75–79. Molecular analysis of the bare lymphocyte syndrome.
Lisowaska-Grospierre, et al. (1985) J. Clin. Invest. 76:381–385. A defect in the regulation of major histocompatibility complex class II gene expression in human HLA-DR negative lymphocytes from patients with combined immunodeficiency syndrome.
Arens, et al. (1987) J. Infectious Diseases 156:837–841. Multiple and persistent viral infections in a patient with bare lyphocyte syndrome.
Clement, et al. (1988) J. Clin. Invest. 81:669–675. Bare lymphocyte syndrome.
Sugiyama, et al. (1986) Chest 89:398–401. Progressive sinobronchiecstasis associated with the "Bare lymphocyte syndrome" in an adult.
Hume, et al. (1989) HumanImmunology 25:1–11. Bare lymphocyte syndrome: altered HLA class II expression in B cell lines derived from two patients.

*Primary Examiner*—Jasemine C. Chambers
*Attorney, Agent, or Firm*—Betram I. Rowland; SaraLynn Mandel; Lucy J. Billings

[57] ABSTRACT

Homologous recombination is employed to inactivate genes, particularly genes associated with MHC antigens. Particularly, the $\beta_2$-microglobulin gene is inactivated for reducing or eliminating Class I MHC antigens. The resulting cells may be used as universal donors. In addition, embryonic stem cells may be modified by homologous recombination for use in producing chimeric or transgenic mammalian hosts, which may be used as source of universal donor organs.

5 Claims, No Drawings

HOMOLOGOUS RECOMBINATION FOR UNIVERSAL DONOR CELLS AND CHIMERIC MAMMALIAN HOSTS

CROSS-REFERENCE TO RELATED APPLICATIONS

This application is a continuation-in-part of application Ser. No. 431,872 filed Nov. 6, 1989, now abandoned, and application Ser. No. 385,651, filed Jul. 25, 1989, now abandoned, and claims priority to PCT/US90/04178, filed Jul. 25, 1990.

INTRODUCTION

1. Technical Field

The field of the subject invention is the use of major histocompatibility complex antigen lacking cells and organs which may serve as universal donors in cellular and organ therapies including transplantation and to produce chimeric non-human mammals.

2. Background

To protect vertebrates from disease and infection, elaborate protective systems have evolved. In mammals, the immune systems serves as the primary defense with many different types of cells and mechanisms to protect the host. A wide variety of hematopoietic cells exist, with the major protective lineages being lymphoid and myeloid. The immune system which results from cells of the lymphoid and myeloid lineages is developed in vivo, so as to recognize self from non-self. Those aberrant situations where the immune system attacks self, such as rheumatoid arthritis, lupus erythematosus, and certain forms of diabetes, are evidence of importance to the host that only foreign agents be attacked. The protective mechanism which protects the host from disease, as a result of invasion of viruses, bacteria, or other pathogens, is also able to recognize cells which come from a different mammalian host, even an allogeneic host.

As part of the system for the self-versus-foreign recognition, the surface membrane protein major histocompatibility complex (MHC) antigens serve an important role. Each host has a personal set of Class I and II MHC antigens, which serve to distinguish that host from other hosts. The lymphoid system is predicated upon recognition of the presence of such MHC antigens as self. Where transplantation from another allogeneic host occurs, unless the transplant is matched with the host or the host is immunocompromised, the transplant may be attacked and destroyed by the immune system. When a transplant occurs which includes lymphocytes, monocytes or progenitors thereof, particularly bone marrow, a graft may attack the host as foreign, resulting in graft-versus-host disease.

There are many situations where one may wish to transplant cells into a recipient host where the recipient's cells are missing, damaged or dysfunctional. When the host is immunocompromised, there may be an interest in transfusing specific white cells, particularly T-cells, which may protect the host from various diseases. When the host lacks the ability to raise a defense against a particular disease, there may also be an interest in administering specific T-cells or B-cells or precursors thereof which may supplement the host's compromised immune system. In other cases, where certain cells are lacking, such as islets of Langerhans in the case of diabetes, or cells which secrete dopamine in the case of Parkinson's disease, or bone marrow cells in various hematopoietic diseases, or muscle cells in muscle wasting disease, or retinal epithelial cells in visual disorders, it would be desirable to be able to provide cells which could fulfill the desired function. In order for the cells to be effective, they must be safe from attack by the host, so that they may function without being destroyed by the immune system. It is therefore of interest to find effective ways to produce cells which may function, proliferate, and differentiate as appropriate, while being safe from attack by a recipient's immune system. The same reasons apply to the use of organs for transplantation including but not limited to the heart, lung, liver and kidney.

There is also substantial interest in being able to study various physiological processes in vivo in an animal model. In many of these situations, one would wish to have a specific gene(s) inactivated or introduced in a site-directed fashion. Where all or a substantial proportion of the cells present in the host would be mutated, the various processes could be studied. In addition, heterozygous hosts having one wild-type gene and one mutated gene could be mated to obtain homozygous hosts, so that all of the cells would have the appropriate modification. Such genetically mutated animals could serve for screening drugs, investigating physiologic processes, developing new products, and the like.

Relevant Literature

A number of papers describe the use of homologous recombination in mammalian cells, including human cells. Illustrative of these papers are Kucherlapati et al., *Proc. Natl. Acad. Sci. USA* 81: 3153–3157, 1984; Kucherlapati et al., *Mol. Cell. Bio.* 5: 714–720, 1985; Smithies et al., *Nature* 317: 230 234, 1985; Wake et. al., *Mol. Cell. Bio.* 8: 2080–2089, 1985; Ayares et al., *Genetics* 111: 375–388, 1985; Ayares et al., *Mol. Cell. Bio.* 7: 1656–1662, 1986; Song et al., *Proc. Natl. Acad. Sci. USA* 84: 6820–6824, 1987; Thomas et al., *Cell* 44: 419–428, 1986; Thomas and Capecchi, *Cell* 51: 503–512, 1987; Nandi et al., *Proc. Natl. Acad. Sci. USA* 85: 3845–3849, 1988; and Mansour et al., *Nature* 336: 348–352, 1988.

Evans and Kaufman, *Nature* 294: 154–146, 1981; Doetschman et al., *Nature* 330: 576–578, 1987; Thomas and Capecchi, *Cell* 51: 503–512, 1987; Thompson et al., Cell 56: 316–321, 1989; individually describe various aspects of using homologous recombination to create specific genetic mutations in embryonic stem cells and to transfer these mutations to the germline. The polymerase chain reaction used for screening homologous recombination events is described in Kim and Smithies, *Nucleic Acids Res.* 16: 8887–8903, 1988; and Joyner et al, *Nature* 338: 153–156, 1989. The combination of a mutant polyoma enhancer and a thymidine kinase promoter to drive the neomycin gene has been shown to be active in both embryonic stem cells and EC cells by Thomas and Capecchi, supra, 1987; Nicholas and Berg (1983) in *Teratocarcinoma Stem Cell*, eds. Siver, Martin and Strikland (Cold Spring Harbor Lab., Cold Spring Harbor, N.Y. (pp. 469–497); and Linney and Donerly, *Cell* 35: 693–699, 1983.

Bare lymphocytes are described in Schuurman et al., The Thymocyte in "Bare Lymphocyte" Syndrome In: Microenvironments in the Lymphoid System, ed. Klaus, G. G. B., Plenum Press, NY, pp. 921–928; Sullivan et al., *J. Clin. Invest.* (1985) 76: 75–79; Lisowska-Grospierre et al., ibid. (1985) 76: 381–385; Arens, et al., *J. Inf. Dis.* (1987) 156: 837–841; Clement et al., *J. Clin.*

Invest. (1988) 81: 669–675; Sugiyama et al., *Chest* (1986) 89: 398–401; and Hume et al., *Human Immunology* (1989) 25: 1–11.

SUMMARY OF THE INVENTION

Cells lacking MHC antigens are provided which may serve as universal donor cells or as embryonic stem cells which may be used to produce chimeric mammals carrying the mutation. The cells may be obtained as a result of a naturally occurring genetic defect or mutation by homologous recombination. Particularly, by inactivating at least one allele of at least one MHC antigen chain, e.g., $\beta_2$-microglobulin, cells can be produced which have reduced capability for expression of MHC antigens and can be further used for complete removal of expression of at least one type of MHC antigen. The resulting cells having reduced expression of MHC antigens may be used as universal donors lacking markers for host (recipient) immune attack. The cells may also be used in vitro to interact with other cells. Chimeric mammals carrying this trait may be used in the study of immunodeficiency and may be used as a source of organs for transplantation between different species.

DESCRIPTION OF SPECIFIC EMBODIMENTS

MHC antigen lacking cells are provided for a variety of purposes. The cells may be obtained as a result of a naturally occurring genetic defect or as a result of homologous recombination. The cells may be further modified by introduction or inactivation of a gene of interest.

Homologous recombination may be employed for inactivation or alteration of genes in a site-directed manner, particularly a gene associated with an MHC antigen. Depending upon the nature of the cell, the cell lacking at least one competent MHC antigen may find use as a donor to an allogeneic host or if an embryonic stem cell, may find use in the production of chimeric mammalian hosts which themselves could be used as a source of organs for transplantation.

Of particular interest is the inactivation of at least one, preferably both, copies of a subunit of an MHC antigen, more particularly, $\beta_2$-microglobulin. Where a mutation in the $\beta_2$-microglobulin gene of an embryonic stem cell is produced, a mammalian host derived from the embryonic stem cell may be used for investigation of the immune system and the role of Class I MHC antigen in that system. Of particular interest are methods which provide for cells lacking at least one MHC antigen, Class I or Class II, preferably Class I, which cells may serve a variety of functions in a viable host. The method involves transfection of mammalian cells, particularly normal cells, of a predetermined species with DNA associated with one of the loci related to the $\beta_2$-microglobulin gene, the $\alpha$-subunit(s) of the Class I or II MHC antigens or the $\beta$-subunit(s) of the Class II MHC antigens. The human Class II MHC antigens are HLA-DR, DP AND DQ, where DR is of primary interest.

The DNA will comprise at least a portion of the gene(s) at the particular locus with introduction of a lesion into at least one, usually both copies, of the native gene(s), so as to prevent expression of a functional MHC antigen molecule. The lesion may be an insertion, deletion, replacement or combination thereof. When the lesion is introduced into only one copy of the gene being inactivated, the cells having a single unmutated copy of the target gene are amplified and may be subjected to a second transformation, where the lesion may be the same or different from the first lesion, usually different, and where a deletion, or replacement is involved, may be overlapping at least a portion of the lesion originally introduced. The resulting transformants are screened for the absence of a functional target antigen and the DNA of the cell may be further screened to ensure the absence of a wild-type target gene. Alternatively, homozygosity as to a phenotype may be achieved by breeding hosts heterozygous for the mutation.

The cells which may be subjected to transformation may be any mammalian cells of interest, which may find use in cell therapy, research, interaction with other cells in vitro or the like. Cells of particular interest include, among other lineages, the islets of Langerhans, adrenal medulla cells which may secrete dopamine, osteoblasts, osteoclasts, epithelial cells, endothelial cells, T-lymphocytes, neurons, glial cells, ganglion cells, retinal cells, embryonic stem cells, liver cells, bone marrow cells, and myoblast (muscle) cells.

Cells from bare syndrome patients may be isolated in accordance with conventional ways, e.g., panning, affinity columns, magnetic beads, or the like. By employing monoclonal antibodies specific for the lymphoid cell type, B- or T-cell, using monoclonal antibodies for such markers as CD 3, 4, 8, 10, 15 or 19, the desired group of cells and their progenitors may be isolated in a substantially homogeneous composition. The genetically defective cells may be used in the same manner as MHC antigen defective cells produced by homologous recombination.

The MHC antigen deficient cells will be selected to achieve a particular function and be introduced into a mammalian host or used for research or other purpose. Also of interest will be the stem cells which act as the progenitors for any of the above cells, which may be the original progenitor or a progenitor cell which is already dedicated to a particular lineage. Of particular interest will be epidermal cells, such as keratinocytes, retinal epithelial cells, myoblasts, hematopoietic cells, and other cells which may be readily manipulated in vitro, maintained for long periods of time in culture and may be introduced into a host, where the cells will remain viable and functional for long periods of time.

For embryonic stem cells, an embryonic stem cell line may be employed or embryonic stem cells may be obtained freshly from a host. The cells may be grown on an appropriate fibroblast-feeder layer or grown in the presence of leukemia inhibiting factor (LIF) and then used for mutation.

The procedures employed for inactivating one or both copies of a particular MHC antigen will be similar, differing primarily in the choice of sequence, selectable marker used, and the method used to identify the absence of the MHC antigen, although similar methods may be used to ensure the absence of expression of a particular antigen. Since the procedures are analogous, the inactivation of the $\beta_2$-microglobulin gene will be used as an example. It is to be understood that substantially the same procedures, but with other genetic sequences, will suffice for the $\alpha$- and $\beta$-subunits of the Class II MHC antigens.

DNA constructs may be employed which provide for the desired introduction of the lesion into the cell. The constructs may be modified to include functional entities other than the mutated sequence which may find use in the preparation of the construct, amplification, transformation of the host cell, and integration of the construct into the host cell. Techniques which may be used include calcium phosphate/DNA coprecipitates, microinjection of DNA into the nucleus, electroporation, bacterial protoplast fusion with intact cells, transfection, or the like. The DNA may be single or double stranded, linear or circular, relaxed or supercoiled DNA. For various techniques for transforming mammalian cells, see Keown et al., Methods in Enzymology (1990) vol. 185, pp. 527–537.

The homologous sequence for targeting the construct may have one or more deletions, insertions, substitutions or combinations thereof. For example, the $\beta_2$-microglobulin may include a deletion at one site and an insertion at another site which includes a gene which may be used for selection, where the presence of the inserted gene will result in a defective inactive protein product. Preferably, substitutions are employed. For an inserted gene, of particular interest is a gene which provides a marker, e.g., antibiotic resistance such as neomycin resistance, including G418 resistance.

The deletion will be at least about 50 bp, more usually at least about 100 bp, and generally not more than about 20 kbp, where the deletion will normally include at least a portion of the coding region including a portion of or one or more exons, a portion of or one or more introns, and may or may not include a portion of the flanking non-coding regions, particularly the 5'-non-coding region (transcriptional regulatory region). Thus, the homologous region may extend beyond the coding region into the 5'-non-coding region or alternatively into the 3'-non-coding region. Insertions will generally not exceed 10 kbp, usually not exceed 5 kbp, generally being at least 50 bp, more usually at least 200 bp.

The homologous sequence should include at least about 100 bp, preferably at least about 150 bp, more preferably at least about 300 bp of the target sequence and generally not exceeding 20 kbp, usually not exceeding 10 kbp, preferably less than about a total of 5 kbp, usually having at least about 50 bp on opposite sides of the insertion and/or the deletion in order to provide for double crossover recombination.

Upstream and/or downstream from the target gene construct may be a gene which provides for identification of whether a double crossover has occurred. For this purpose, the herpes simplex virus thymidine kinase gene may be employed, since the presence of the thymidine kinase gene may be detected by the use of nucleoside analogs, such as Acyclovir or Gancyclovir, for their cytotoxic effects on cells that contain a functional HSV-tk gene. The absence of sensitivity to these nucleoside analogs indicates the absence of the thymidine kinase gene and, therefore, where homologous recombination has occurred that a double crossover event has also occurred.

The presence of the marker gene inserted into the $\beta_2$-microglobulin gene establishes the integration of the target construct into the host genome. However, DNA analysis will be required in order to establish whether homologous or non-homologous recombination occurred. This can be determined by employing probes for the insert and then sequencing the 5' and 3' regions flanking the insert for the presence of $\beta_2$-microglobulin extending beyond the flanking regions of the construct or identifying the presence of a deletion, when such deletion is introduced.

The polymerase chain reaction may be used with advantage in detecting the presence of homologous recombination. Primers may be used which are complementary to a sequence within the construct and complementary to a sequence outside the construct and at the target locus. In this way, one can only obtain DNA duplexes having both of the primers present in the complementary chains if homologous recombination has occurred. By demonstrating the presence of the primer sequences or the expected size sequence, the occurrence of homologous recombination is supported.

The construct may further include a replication system which is functional in the mammalian host cell. For the most part, these replication systems will involve viral replication systems, such as Simian Virus 40, Epstein-Barr virus, papilloma virus, adenovirus and the like.

Where a marker gene is involved, as an insert, and/or flanking gene, depending upon the nature of the gene, it may have the wild-type transcriptional regulatory regions, particularly the transcriptional initiation regulatory region or a different transcriptional initiation region. Whenever a gene is from a host where the transcriptional initiation region is not recognized by the transcriptional machinery of the mammalian host cell, a different transcriptional initiation region will be required. This region may be constitutive or inducible, preferably inducible. A wide variety of transcriptional initiation regions have been isolated and used with different genes. Of particular interest as promoters are the promoters of metallothionein-I and II from a mammalian host, thymidine kinase, $\beta$-actin, immunoglobulin promoter, human cytomegalovirus promoters, and SV40 promoters. In addition to the promoter, the wild-type enhancer may be present or an enhancer from a different gene may be joined to the promoter region.

The construct may further include a replication system for prokaryotes, particularly E. coli, for use in preparing the construct, cloning after each manipulation, allowing for analysis, such as restriction mapping or sequencing, followed by expansion of a clone and isolation of the plasmid for further manipulation. When necessary, a different marker may be employed for detecting bacterial transformants.

Once the vector has been prepared, it may be further manipulated by deletion of the bacterial sequences as well as linearization, where a short deletion may be provided in the homologous sequence, generally not exceeding about 500 bp, generally being from about 50 to 300 bp. The small deletion will generally be near one or other end of the targeted structural gene.

Once the construct has been prepared and manipulated and the undesired sequences removed from the vector, e.g., the undesired bacterial sequences, the DNA construct is now ready to be introduced into the target cells. As already indicated, any convenient technique for introducing the DNA into the target cells may be employed. After transformation of the target cells, many target cells are selected by means of positive and/or negative markers, as previously indicated, neomycin resistance and Acyclovir or Gancyclovir resistance. Those cells which show the desired phenotype may then be further analyzed by restriction analysis, electrophoresis, Southern analysis, polymerase chain reaction or the like. By identifying fragments which show the presence of the lesion(s) at the target gene site, one can identify cells in which homologous recombination has occurred to inactivate one of the two copies of the target gene.

The second construct will differ from the first construct in not necessarily requiring a marker for selection, since the absence of the target MHC antigen on the surface of the cells may be used as a marker. Thus, one may again use insertions, deletions or replacements as lesions for modifying and inactivating the target gene. Similarly, one may detect the absence of a Class II MHC antigen on the surface as evidence of the absence of expression of the particular Class II MHC antigen.

Transformation of the cells in which one of the copies has been inactivated may then be performed in the same or different way from the previous method of transformation. The resulting transformed cells may then be selected by the absence of the target MHC antigen on the surface of the cell. This can be achieved in a variety of ways. For example, one may use antibodies to any epitope of the target MHC antigen in conjunction with complement to kill any cells having the antigen. Alternatively, one may use conjugates of the appropriate antibody, particularly monoclonal antibody with a toxin, such as the A chain of ricin, abrin, diphtheria toxin, or the like. Affinity chromatography may be employed, where antibodies may be used to remove cells comprising the target antigen. The resulting cells which survive should be free of at least one MHC antigen on their surface and now not be as subject to transplant rejection when introduced in vivo as wild-type cells.

The resulting cells will then be screened to ensure that substantially no Class I MHC antigens are on the surface. This may be achieved as described above by selecting for cells lacking the Class I MHC antigen. The cells may then be grown in an appropriate nutrient medium for expansion and used in a variety of ways. For example, with keratinocytes, the cells may be used for replacement of skin in the case of burns, where keratinocytes may be grown to form a continuous layer prior to application. Similarly, the keratinocytes may be used in the case of plastic surgery to replace skin removed from the host for use at another site. Other uses for the keratinocytes include transplantation in decubitus ulcers.

In the case of islets of Langerhans, they may be grown and introduced into capsules or otherwise for insertion into a host for the production of insulin. In the case of retinal epithelial cells, they may be injected into the subretinal space of the eye to treat visual disorders, such as macular degeneration. In the case of immune cells, they may be injected into the bloodstream or elsewhere to treat immune deficiency. In the case of myoblasts, they may be injected at various sites to treat muscle wasting diseases, such as Duchenne muscular dystrophy.

The genes which are introduced may also serve for protein production, where the proteins may be retained intracellular or be secreted. Production of proteins may include growth factors such as, e.g., G-, M-, and GM-CSF, epidermal growth factor, platelet derived growth factor, transforming growth factor, etc; lymphokines, such as the interleukins; hormones, such as ACTH, somatomedin, insulin, angiotensin, etc., coagulation factors, such as Factor VIIIC; normal versions of the proteins associated with genetic diseases such as adenosine deaminase or the protein associated with cystic fibrosis; protective agents, such as $\alpha_1$-antitrypsin; regulatory proteins or enzymes associated with the production of amino acid free products, such as the expression of tyrosine hydroxylase for the production of L-dopamine, and the like. The genes may be under the transcriptional control of a constitutive promoter or inducible promoter (including enhancer sequence). In the latter situation, regulation may result by induction by a naturally occurring signal or as a result of introduction into the host of an exogenous signal.

Depending upon the nature of the cells, the therapy involved, and the disorder, the cells may be employed as films, introduced in containers for maintenance at a particular site, or as solid masses impregnated in inert matrices or independent of a matrix. The number of cells administered will vary widely, depending upon the particular application and the manner in which the cells are administered.

Administration may be by injection, typical application, incision and placement, in the appropriate location.

For embryonic stem cells, after mutation, the cells may be plated onto a feeder layer in an appropriate medium, e.g., fetal bovine serum enhanced DMEM. Cells containing the construct may be detected by employing a selective medium and after sufficient time for colonies to grow, colonies may be picked and analyzed for the occurrence of homologous recombination. As described previously, the polymerase chain reaction may be used, with primers within and without the construct sequence but at the target locus. Those colonies which show homologous recombination may then be used for embryo manipulating and blastocyst injection. Blastocysts may be obtained from 4 to 6 week old superovulated females by flushing the uterus 3.5 days after ovulation. The embryonic stem cells may then be trypsinized and the modified cells added to a droplet containing the blastocysts. At least one, usually at least about 10, and up to about 30 of the modified embryonic stem cells may be injected into the blastocoel of the blastocyst. After injection, at least one and not more than about 15 of the blastocysts are returned to each uterine horn of pseudopregnant females. Females are then allowed to go to term and the resulting litters screened for mutant cells having the construct. The blastocysts are selected for different parentage from the transformed ES cells. By providing for a different phenotype of the blastocyst and the ES cells, chimeric progeny can be readily detected. A particularly useful phenotype is hair color, although any phenotype may be used or, if desired, one may look to genotype, probing for the presence of the modified genomic DNA.

The pups will usually be born 16–18 days after introduction of the blastocysts into foster mothers. The chimeric animals are screened for the presence of the transformed genome and males and females comprising the transformed genome are mated. The homozygous progeny lack Class I MHC cells and mature CD8 T-cells (TCR $\alpha\beta$).

The mammals may be any non-human mammal, such as laboratory animals, domestic animals, pets, etc.

The mammals which lack Class I MHC may be used as a source of organs for transplantation such as heart, lung, liver and kidney.

The following examples are offered by way of illustration and not by way of limitation.

EXPERIMENTAL

Proliferation of Epidermal Keratinocytes Lacking MHC Antigen Due to Inactivation of $\beta_2$-microglobuile Gene Expression Cells Mouse epidermal keratinocytes are obtained from the skin of a newborn mouse. The skin samples are rinsed in serum-free medium and minced into small fragments. The fragments are treated with trypsin and the resulting single cell suspension washed and plated on 3T3 fibroblast feeder layers. EGF (5 ng/ml) is added at the end of five days. The cells are maintained in media supplemented with hydrocortisone ($10^{-6}$M), cholera toxin ($10^{-7}$M), insulin (5 ng/ml), transferrin (5 ng/ml) T3 ($2 \times 10^{-8}$M) and 20% fetal calf serum. Unused cells are stored in liquid nitrogen.

Human epidermal keratinocytes are isolated using a fresh skin sample from a circumcised skin as the source of the keratinocytes. The sample is then treated substantially as described above.

DNA Vectors

The mouse and human $\beta_2$-microglobulin genes as isolated and characterized by Parnes and Seidman, *Cell*, 29: 661-669, (1982), and Gusow et al., *J. Immunol.*, 139: 3132-3138 (1987), respectively, are employed for homology.

Construction of Inactivation Vector 1

The inactivation vectors are constructed from 4 kb HindIII fragment of the genomic DNA which encompasses the second, third and fourth exons of the $\beta_2$-microglobulin gene. The 4 kb HindIII subcloned into pBR322 is digested with EcoRI and the selectable neomycin phosphotransferase (neoR) gene inserted. The neo$^R$ gene is obtained from pSV2neo (Southern and Berg, *Mol. Appl. Genet.*, 1: 332, (1982)). The resulting vector is called B2KO1.

Construction of Inactivation Vector 2

The starting plasmid for the construction of the second vector is B2KO1. In this case, the herpes simplex virus type 1 thymidine kinase gene is inserted at the HindIII site of B2KO1.

Inactivation of One Copy of $\beta_2$-microglobulin

The DNA which is used for transformation in the first or second stage comprises the inserted sequence with flanking homologous sequences from the cloning plasmid B2KO1 and the same sequence flanked at one end by tk gene free of the bacterial plasmid DNA. The resulting DNA fragments are purified by ethanol precipitation and cleared by passage through a 0.22 micron filter. The DNA is isolated by conventional means and introduced into the keratinocyte cells by microinjection (Capecchi, *Cell*, 22: 479-488 (1980). Approximately 5-50 copies of the DNA constructs are injected into each nucleus. The cells are then grown in selective medium comprising 200 µg/ml of G418 (Geneticin, Gibco Labs). For the second construct, the cells are also plated in Gancyclovir (Syntex Corp, Palo Alto, Calif.) or Ayclovir (Burrows-Wellcome, Research Triangle Park, N.C.). Cells from colonies are isolated and analyzed by the polymerase chain reaction and Southern blot hybridization. Cells demonstrating one copy of the $\beta_2$-microglobulin being inactivated are used for knocking out the second copy.

Inactivation of The Second Copy of the $\beta_2$-microglobulin Gene

Gene

Cells obtained from above with a single inactivated $\beta_2$-microglobulin gene are microinjected as described above with the modified B2K02 plasmid and cells resistant to Gancyclovir or Acyclovir isolated. Cells which lack Class I gene expression are isolated by combining the cells with monoclonal antibodies specific for $\beta_2$-microglobulin and complement as described by Parish et al., (1974), *Eur. J. Immunol.*, 4: 808. Resulting viable cells are grown in selected medium and passed through an affinity column of the same monoclonal antibodies. The column is prepared as described by Harlow and Lane, (1988), *Antibodies: A Laboratory Manual*, CSH Press. Southern blot analysis of the cells is performed to establish the proper locus of integration. The cells are then expanded and stored for further use.

Generation of Monolayer of Keratinocytes

The resulting cells lacking Class I MHC are used to grow a monolayer of keratinocytes as described by Rheinwald and Green, *Cell* 6: 331-343, (1975). This layer is transplanted onto allogenic mice as described by Rheinwald and Green, (1975), supra. The cells adhere to the surface and grow to provide a protective skin layer.

Following the same procedure as described above for $\beta_2$-microglobulin the HLA-DR genes may be inactivated by employing homologous sequences flanking the α-subunit of the HLA-DR gene of the host cell. In this way cells which have the Class II MHC antigen or may have the capability to have the expression of such antigen induced are prevented from expressing the primary Class II antigen associated with the cellular immune response.

In the next study, embryonic stem cells were modified by homologous recombination with one of the $\beta_2$-microglobulin genes.

Materials and Methods

Construction of the Targeting Plasmid

The plasmid pKC$\beta_2$B contains the entire $\beta_2$m gene within an 8.4 kbp XhoI fragment (Ozato and Orrison, *Proc. Natl. Acad. Sci. USA*, 82: 2427-2431, (1985); Warner et al., *Bio. Reprod.*, 36: 611-616, (1987). The 5'XhoI to BamHI fragment of this gene was subcloned into pUC19. Two KpnI restriction enzyme sites, one in the 5' flanking DNA and the other within the first intron, were removed by digestion with KpnI followed by treatment with T4 polymerase and religation. A unique ClaI site was created in exon 2 by partial digestion with EcoRI followed by treatment with Klenow polymerase and ligation with ClaI linkers. The 1150 bp XhoI to HI fragment of the plasmid pMC1 Neo (Kim and Smithies, *Nucleic Acid Res.*, 16: 8887-8903, (1988)), containing a neomycin gene driven by the Herpes simplex virus thymidine kinase gene (HSVtk) promoter and a polyoma enhancer, was inserted via linkers into this ClaI site. Two plasmids, C65.2.3 and C65.5.9, were obtained that differed in the transcriptional orientation of the inserted fragment with respect to that of the $\beta_2$-microglobulin gene. The 5' XhoI to KpnI fragment of each of these was cloned into pUC19 in order to obtain the targeting vectors used in our experiments. In plasmid C84.4B the 5' to 3' orientation of the neomycin and $\beta_2$m promoters is identical. The opposite configuration occurs in plasmid C84.2D.

Culturing, Electroporation, and Selection of ES Cells

The ES cell line E14TG2a (Sawicki et al., *Nature*, 294: 450-451, (1981)), was cultured on mitomycin-treated primary embryonic fibroblast-feeder layers essentially as described (Ostrand-Rosenberg et al., *Proc.*

*Natl. Acad. Sci.* 86: 5084–5088, (1989)). The embryonic fibroblasts were prepared from embryos from C57BL/6 females that had mated 14 to 17 days earlier with a male homozygous for a neomycin transgene (Evans and Kaufman, *Nature,* 292: 154–156, (1981)); these cells are capable of growth in media containing G418. Electropotation conditions were similar to those that have been described previously (Doetschman et al., *Nature,* 330: 576–578, (1987)). ES cells were trypsinized, resuspended in culture media at a concentration of $4 \times 10^7$/ml and electroporated in the presence of the targeting DNA at a concentration of 12 nM in the first experiment and 5 nM DNA in the second. A voltage of 300 V with a capacitance of 150–250 $\mu$F was found optimal with an electroporation cell of 5 mm length and 100 mm$^2$ cross section. $5 \times 10^6$ electroporated cells were plated onto mitomycin-treated fibroblasts in 100 mm dishes in the presence of Dulbecco's modified Eagle's media (DMEM) supplemented with 15% fetal bovine serum (FBS) and 0.1 mM 2-mercaptoethanol. The media was replaced 24 hr after electroporation with media containing 200 $\mu$g/ml G418.

Analysis of G418 Resistant ES Cell Colonies

ES colonies visible 10–14 days after electroporation were picked with drawn out capillary pipettes for analysis using the polymerase chain reaction (PCR). Half of each picked colony was saved in 24-well plates already seeded with mitomycin-treated feeder cells. The other halves, combined in pools of 3–4, were transferred to Eppendorf tubes containing approximately 0.5 ml of PBS and analyzed for homologous recombination by PCR. Conditions for PCR reactions were essentially as described (Linney and Donerly, *Cell,* 35: 693–699, (1983)). The ES cells were pelleted, resuspended in 5 $\mu$l of phosphate buffered saline (PBS), and lysed by the addition of 55 $\mu$l of H$_2$O to each tube. DNAses were inactivated by heating each tube at 95° C. for 10 min. After treatment with proteinase K at 55° C. for 30 min, 30 $\mu$l of each lysate was transferred to a tube containing 20 $\mu$l of a reaction mixture including PCR buffer, 1.5 $\mu$g of each primer, 3U of Taq polymerase, 10% DMSO, and dATP, dCTP, dGTP and dTTP each at 0.2 mM. PCR was carried out for 55 cycles using a thermocycler modelled after one described previously (Kim and Smithies, supra, (1988)), with 65 seconds melt at 92° C. and a 10 min annealing and extension time at 65° C. The two priming oligonucleotides, TGGCGGACCG-CTATAGGAC and GATGCTGAT-CACATGTCTCG, correspond respectively to sequences located 650 bases 3' of the start codon of the neomycin gene and sequences located in exon 3 of the $\beta_2$m gene. 20 $\mu$l of the reaction mix was electrophoresed on agarose gels and transferred to nylon membranes (Zeta Bind). Filters were probed with $^{32}$P-labelled 450 bp EcoRI to KpnI fragment of the $\beta_2$m gene.

Preparation and Restriction Enzyme Analysis of Genomic DNA

Genomic DNA was prepared from ES cells, whole new born mice, and mouse tails by conventional methods. DNA was digested with restriction enzymes as directed by the manufacturers and fragments were separated on 0.7% agarose gels. DNA was transferred to nylon membranes and probed with the $^{32}$p labelled fragment described above.

Embryo Manipulation and Blastocyst Injection

Mice were purchased from either Jackson Laboratories (Bar Harbor, Me.) or Charles River (Raleigh, N.C.). C57BL/6 blastocysts were obtained from 3 to 4 week old superovulated females. Uteri were flushed with M2 media (Joyner et al., *Nature,* 338: 153–156, (1989)), 3.5 days after ovulation. Blastocysts were collected, washed several times in fresh M2 media, and placed in a 100 $\mu$l droplet of M2 under paraffin oil. ES cells were trypsinized, washed once with fresh DMEM media and diluted to approximately $2 \times 10^6$ cell/ml. 5 $\mu$l of cells were added to the droplet containing the blastocysts. 10 to 15 ES cells were injected into the blastocoel of each blastocyst. Following injection 6 to 9 blastocyst were returned to each uterine horn of pseudopregnant females mated 2.5 days previously with vasectomized males. Both C57BL/6$\times$DBA F$_1$ and C57BL/6$\times$CBA F$_1$ mice proved to be excellent foster mothers, yielding a pregnancy rate close to 100% and able to raise small litters.

Isolation and Characterization of Targeted ES cells

Two independent targeting experiments were carried out. In each, $2 \times 10^7$ cells were electroporated in the presence of the incoming DNA, and were then cultured in media containing G418. After about two weeks, G418 resistant colonies were readily apparent. A portion of each colony was then transferred to an individual well of a 24-well plate, while the remaining portion was pooled with portions from two to four other colonies for PCR analysis. In the first experiment, one pool gave a positive PCR signal out of 32 pools that included a total of 100 G418 resistant colonies. The three individual colonies that had contributed to this positive pool were analyzed individually by PCR, and a positive clone, ES39B, was identified. Similar analysis of 134 G418 resistant colonies obtained in the second experiment also yielded a clone, ES22A, which generated the 910 bp DNA fragment indicating successful targeting when subjected to PCR.

In order to verify the targeted disruption of one copy of the $\beta_2$m gene, (the gene is autosomal and present in two copies), the two PCR positive clones, ES39B and ES22A, were expanded, and their DNA was isolated and then analyzed by Southern blotting using a probe that detects sequences from the second exon and part of the first intron of the $\beta_2$m gene. Patterns obtained with the restriction enzymes XbaI, BamHI and KpnI match those expected if one of the two copies of the $\beta_2$m gene had been disrupted in the planned manner in the PCR-positive clones. That is, one DNA fragment identical in size to that present in untreated cells, was present in untreated cells, but of decreased intensity in the PCR positive clones, with all three enzymes. An additional fragment of the size predicted for a homologous recombination event was present only in the PCR-positive clones. The insertion of the neomycin gene in the second exon by the recombination results in an XbaI fragment detectable with the $\beta_2$m specific probe that is approximately 1 kb longer than the equivalent fragment in the native locus. A new BamHI site is introduced into the locus by the targeting DNA, reducing the size of the BamHI fragment detected by the $\beta_2$m probe from 10.6 kbp to 900 bp. A new fragment is also seen after KpnI digestion. In ES39B the KpnI fragment is 7 kb in length, as predicted by a crossover between the 5' end of the targeting plasmid and the native locus. In ES22A this new KpnI fragment is 4.0 kb in length, which indicates that the deleted KpnI sites were not incorporated into the locus. This observation indicates that one of the crossovers in cell line ES22A resolved between the third KpnI site of the native locus and the inserted neomycin gene of the incoming DNA, presumably after branch migration of a crossover intermediate. Although the 5' crossover sites differ, both modified cell lines now contain a $\beta_2$m gene disrupted in the planned way by insertion of a neomycin gene in exon 2. Re-hybridization of the filter used for the autoradiography with a probe for the neomycin gene shows that the only bands that hybridize are those predicted by the structure of the construct.

Chimeric Offspring of Targeted ES Cells

The two ES cell lines carrying the inactivated $\beta_2$m genes are expected to allow the introduction of this mutation into the mouse germline. Toward this end, we injected 10 to 15 cells into C57BL/6 blastocysts. Embryos were reimplanted into pseudopregnant females. Because the ES cell line E14TG2a was isolated from strain 129/Ola embryos, it and all cell lines derived from it are expected to carry the coat color markers characteristic of this mouse strain. These include the dominant $A^w$ allele at the agouti locus, the recessive chinchilla allele at the c-locus, and the recessive p-allele (pink-eyed dilution) at the p-locus (Quinn et al., *J. Reprod. Fertil.*, 66: 161–168, (1981)). Contribution of ES cells to the mesoderm-derived portions of hair follicles results in an agouti coat. Hair follicles to which melanocytes of ES cell origin (and therefore carrying the p and $c^{ch}$ mutations) have migrated produce cream-colored hairs. Both of these coat colors are easily distinguished from the solid black coat seen in pups derived from non-agouti C57BL/6 host blastocysts.

More than 70% of surviving pups are chimeras. The intensity of the 6.1XbaI band diagnostic of the targeted $\beta_2$m locus shows that the modified ES cells contributed extensively to the tissue of this animal.

Generation of Chimeric Mice

Three to four week old C57BL/6 female mice were superovulated by the sequential injection of PMS and hCG and mated with fertile males of similar strain. Four days after mating, the female mice were sacrificed, and blastocysts obtained by flushing the uterus with M9 media. The collected blastocysts were transferred to a droplet of the same media that was submerged in paraffin oil and also contained some ES22a cells. These cells had been prepared for injection by trypsinization followed by washing and resuspending in M2 media. Ten to fifteen ES22a cells were introduced into the blastocoel of each blastocyst using standard micromanipulation techniques. The ES cell containing blastocysts were then transferred to the uterus of a pseudopregnant foster mother. Foster mothers were obtained by mating B6/D2 females with vasectomized male mice. Females which had mated 2.5 days prior to the date of transfer, as asserted by the presence of a vaginal plug were used as foster mothers for the ES cell containing blastocysts. Development of the blastocysts continues in vivo and pups were generally born 16-18 days later. The contribution of the ES cells to the offspring could be judged visually by examination of the coat color of the pups. The blastocysts were obtained from C57BL/6 mice, which are solid black in color. The ES cell line E14T-G2a, the parental line from which ES22a was derived was isolated from 129/Ola mice. This mouse strain is cream in color, the combined effect of three coat color genes, the dominant $A^w$ allele at the agouti locus, recessive pink-eyed-dilute allele at the p locus and the recessive $c^{ch}$ at the C locus. Offspring in which the ES22a had participated in the formation of the animal had coats containing brown and cream hairs. About 80% of the pups from blastocysts containing ES22a cells showed some degree of coat color chimerism.

Generation of Animals Heterozygous for the Mutated $\beta_2$m Gene

If ES22a cells contribute to the gonads the animals would be expected to generate sperm which contain the ES22a genome and pass it on to its offspring. The ES22a genome is homozygous for the dominant color coat marker $A^w$. If the chimera is mated with an animal that is non-agouti such as a C57BL/6 or B6/D2, offspring that arise from sperm or ES cell origin can be distinguished from those derived from sperm or blastocyst origin by their coat color. 50% of these agouti animals would be expected to inherit the mutated $\beta_2$m gene. These can be identified by analysis of DNA isolated from the tails. 1 cm of tail was therefore removed from the agouti animals, and DNA prepared by standard techniques. DNA was digested with either the restriction enzyme XbaI or HindIII and analyzed by Southern blotting and probing with a radioactively labelled fragment of the $\beta_2$m gene. The presence of an XbaI or HindIII fragment 1 Kb larger than that found in control mice is indicative of the presence of the mutated $\beta_2$m gene in the animal.

Generation of Animals Homozygous for the Mutated $\beta_2$m Gene

Male and female animals whose DNA indicated that they were carrying one copy of the mutated $\beta_2$m gene were mated. Offspring of these matings were again analyzed for the presence of the larger XbaI or HindIII fragments. As expected one quarter of the offspring from such matings were homozygous for the defective gene. These animals now represent a new mouse strain which carries the mutation that was originally introduced by homologous recombination into the ES cell E14TG2a.

Determination of the Phenotype of the $\beta_2$m $-/-$ Mice

To determine whether as expected, the mutation of the $\beta_2$m protein resulted in loss of class I expression, two animals homozygous for the $\beta_2$m mutation were sacrificed and examined for the presence of cell surface class I expression. Cells isolated from lymph node, spleen and thymus were examined with monoclonal antibodies directed against the Class I antigens H-2K$^b$ and H-2Db. Both 129/Ola, the mouse strain from which the ES cell line was derived and C57BL/6 the strain with which the chimera giving rise to these animals had been mated, express the H-$2^b$ haplotype. No staining above background was seen with cells obtained from the homozygous $\beta_2$m $-/-$ mice in any of the tissues examined. Therefore, as predicted, the inactivation of $\beta_2$m gene resulted in an animal that fails to express Class I antigens at the cell surface. The animals appeared healthy and could not be distinguished visibly from their litter mates.

The effect of lack of class I antigens on the maturation of T-cells was examined by isolating and staining thymocytes with antibodies that delineate various stages of T-cell differentiation. The data showed that the CD4−8−, CD4+8+, and CD4+8− cell populations in the thymuses of normal, $\beta_2$m $-/-$, and heterozygous animals are identical. In contrast, the CD4−8+ populations differ between animals of the different genotypes. CD4−8+ cells represent 10% of the cells of the normal thymus but less than 1% of the cells in the thymus of the $\beta_2$m mice. Interestingly, the number of these cells in the heterozygote is also somewhat reduced.

To determine whether the absence of the Class I genes affected the maturation of T-cells as indicated by the expression of the T cell receptor genes, thymocytes were stained with antibodies directed against either TCR$\alpha\beta$ or TCR$\gamma\delta$ receptor. No significant difference in the profile of $\alpha\beta$ cell receptor positive cells was seen in $\beta_2$m $-/-$ animals compared to normal, indicating that Class I antigens are not needed for the maturation of thymocytes to TCR bearing CD4+8+, or CD4+8− cells.

Next, peripheral T-cells were examined for expression of $\alpha\beta$ TCR and CD4 and CD8. The yields of T-cells bearing $\alpha\beta$ TCRs from the spleen and lymph nodes of animals lacking $\beta_2$m were not significantly different from those of normal littermate controls. Between 20% and 32% of all T-cells bearing $\alpha\beta$ TCRs also bore CD8 in $\beta_2$m +/+ and +/− animals. Although CD4−, CD8+ thymocytes were somewhat depleted in $\beta_2$m heterozygous animals, the level of peripheral CD8+ T-cells in these mice were comparable to those of normal littermates. By contrast, virtually none of the $\alpha\beta$ TCR-bearing T-cells expressed CD8 in animals homozygous for the $\beta_2$m mutation. A preliminary experiment was done to find out whether the few $\alpha\beta$ T-cells which appeared CD8+ in mutant mice were due to noise in the staining procedures. T-cells from these animals were therefore grown for several days on plastic coated with anti-CD3 antibody and in interleukin-2, a procedure which often stimulates the proliferation of CD8+ T-cells preferentially. CD8 bearing $\alpha\beta$+ T-cells did not appear in greater numbers after such treatment, although $\gamma\delta$ bearing T cells did grow out. The conclusion is that CD8+, $\alpha\beta$ cells are virtually absent in animals which lack Class I MHC expression.

Thymocytes and T-cells from spleen and lymph node were also examined for expression of $\gamma\delta$ TCRs. The numbers of these cells were similar in $\beta_2$m $-/-$ mice and controls. An outgrowth experiment (described above) showed that the $\gamma\delta$-bearing cells from $\beta_2$m could proliferate and, moreover, preliminary examination of these cells indicated that about a quarter of them bore CD8. Therefore these studies indicate that $\gamma\delta$ T-cells may not require Class I expression for their existence, even if they also bear CD8.

In accordance with the above results, cells can be provided which will not be subject to immune destruction as a result of the presence of Class I MHC antigens. The cells may find wide use, since they will not be subject to immune attack when introduced into an allogeneic host, while they will still be capable of functioning in their native manner. In this way, a wide range of diseases resulting from the loss of number and/or function of cells may be treated, where the introduced cells will survive, multiply and function. Therefore, not only may diseases as a result of burns, abrasions, pathogens or the like be treated, but also diseases as a result of genetic defects.

Also, embryonic stem cells may be modified by homologous recombination to provide for chimeric mammalian hosts. The chimeric mammalian hosts may then be selected and used for breeding to produce homozygous hosts lacking the inactivated gene and may then be used as a source of organs for transplantation.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of producing a genetically engineered mouse lacking functional Class I major histocompatibility complex antigens, said method comprising:
   (a) transforming mouse embryonic stem cells with a DNA construct comprising a marker gene and at least 100 bp of DNA sequence homologous with a sequence of the endogenous $\beta_2$-microglobulin gene present in a chromosome of said embryonic stem cells, where said construct becomes integrated into said chromosome by homologous recombination, thereby inactivating said $\beta_2$-microglobulin gene;
   (b) selecting for mouse embryonic stem cells which carry said inactivated $\beta_2$-microglobulin gene to provide selected cells;
   (c) introducing said selected cells into the blastocyst of a developing mouse embryo;
   (d) allowing said embryo to develop to term;
   (e) identifying at least one offspring which carries said inactivated $\beta_2$-microglobulin gene in the germ line; and
   (f) breeding said offspring to produce a homozygous mouse lacking functional Class I major histocompatibility complex antigens.

2. A method according to claim 1, wherein said selecting is by means of said marker gene and use of the polymerase chain reaction.

3. A method according to claim 2, wherein said polymerase chain reaction employs two primers, wherein one primer is complementary to a sequence within said construct and the other primer is complementary to a sequence external to said construct but within said $\beta_2$-microglobulin gene.

4. A genetically engineered mouse characterized by inactivation of the $\beta_2$-microglobulin gene and lacking functional Class I major histocompatibility complex antigens, which mouse is produced as a result of:
   (a) inactivating the $\beta_2$-microglobulin gene via homologous recombination in an embryonic stem cell;
   (b) introducing said cell into the blastocyst of a developing mouse embryo;
   (c) allowing said embryo to develop to term;
   (d) identifying at least one offspring which carries said inactivated $\beta_2$-microglobulin gene in the germ line; and
   (e) breeding said offspring to produce a homozygous mouse lacking functional Class I major histocompatibility complex antigens.

5. A mouse according to claim 4, wherein said inactivation comprises insertion of a neo gene.

* * * * *